United States Patent

Mathison et al.

[11] 4,232,014
[45] Nov. 4, 1980

[54] AMINOALKYLINDANS AND USE AS HYPOTENSIVE AGENTS

[75] Inventors: Ian W. Mathison, Big Rapids, Mich.; William E. Solomons, Martin, Tenn.

[73] Assignee: Marion Laboratories, Inc., Kansas City, Mo.

[21] Appl. No.: 3,046

[22] Filed: Jan. 12, 1979

[51] Int. Cl.³ ............... A61K 31/165; A61K 31/135; C07C 103/20; C07C 87/28
[52] U.S. Cl. ................................ 424/324; 424/330; 564/170; 564/177; 564/182; 564/185; 564/374
[58] Field of Search ........... 260/558 P, 559 S, 559 R, 260/570.8 R; 424/324, 330

[56] References Cited

PUBLICATIONS

J. Pharm. Sciences, 67, 314, Mar. 1978.
J. Org. Chem., 39, 2852, (1974).

Primary Examiner—Frederick E. Waddell
Attorney, Agent, or Firm—Merriam, Marshall & Bicknell

[57] ABSTRACT

Aminoalkylindans of the formula

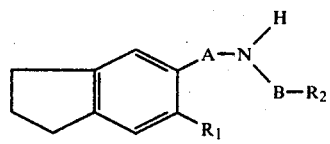

wherein A represents an alkylene group having 2 to 5 carbons in a straight chain, $R_1$ represents a lower alkyl having 1 to 3 carbons or is a lower alkoxy having 1 to 3 carbons, B represents —$CH_2$— or

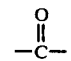

and $R_2$ represents phenyl or phenyl-lower alkyl and the phenyl group in such substituents is unsubstituted or is substituted with 1 to 3 lower alkoxy groups, and acid addition salts of the amines.

The compounds have hypotensive activity.

12 Claims, No Drawings

AMINOALKYLINDANS AND USE AS HYPOTENSIVE AGENTS

This invention relates to aminoethylindans. More particularly, this invention is concerned with novel N-substituted aminoalkylindans, pharmaceutical compositions containing at least one such compound, and the use of the compounds as hypotensive agents. It is also concerned with the discovery that the old compound 5-aminoethyl-6-methylindan has hypotensive properties.

According to one aspect of the present invention there are provided novel N-substituted aminoalkylindans of the formula

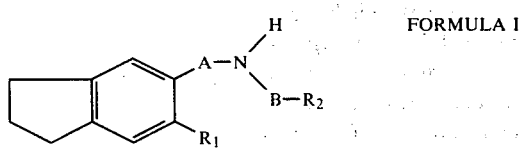

FORMULA I wherein A represents an alkylene group having 2 to 5 carbons in a straight chain, $R_1$ represents a lower alkyl having 1 to 3 carbons or a lower alkoxy having 1 to 3 carbons, B represents —$CH_2$" or

and $R_2$ represents phenyl or a phenyl-lower alkyl and the phenyl group in such substituents is unsubstituted or is substituted with 1 to 3 lower alkoxy groups such as methoxy and ethoxy, and acid addition salts of the amines. The phenyl-lower alkyl substituent represented by $R_2$ will generally have an alkyl with 1 to 2 carbons in a straight chain.

In the above Formula I, A represents, for example, 1,2-ethylene, 1,3-propylene, 1,4-butylene and 1,5-pentylene.

Representative of the groups $R_1$ exemplifies are methoxy, ethoxy, propoxy and isopropoxy.

$R_2$ in the above Formula I, for example, can represent, in addition to phenyl, the groups 4-methoxyphenyl, 3,4-dimethoxyphenyl and 3,4,5-trimethoxyphenyl.

It is to be understood that the subject invention pertains only to compounds of Formula I which are producible and useful and does not include compounds which may come within the formula which for any reason cannot be produced.

The inventions of the subject application have been published, in part, in J. Pharm Sciences, 67, 314 (March, 1978).

The compounds of Formula I above are produced by at least two separate processes, both of which use the same starting materials.

According to one of the processes, a 6-alkyl or alkoxy 5-aminoalkylindan is reacted with an appropriate acyl chloride in the presence of a base to produce the desired 6-alkyl or alkoxy-5-acylaminoalkylindan. This reaction can be represented as follows:

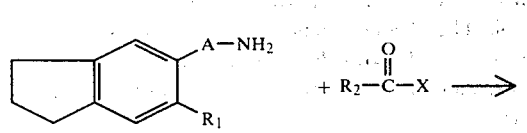

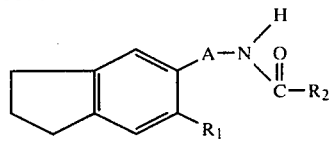

wherein A, $R_1$ and $R_2$ have the significance assigned above and X is a reactive halo group and particularly is a chloro or bromo group.

The 5-aminoalkyl-6-alkyl or alkoxyindan starting materials can be produced by methods disclosed in the prior art. Specifically, 5-aminoethyl-6-methyl and 5-aminoethyl-6-methoxyindan are disclosed in J. Org. Chem., 39, 2852 (1974) as well as methods of preparing those compounds. British patent 1,133,457 discloses 5-methoxy-6-(2-aminopropyl)-indane, related homologs and position isomers and methods of producing such compounds.

Specific 5-aminoalkyl-6-alkyl or alkoxyindans which can be used in the described process are 5-aminoethyl-6-methylindan, 5-(3-aminopropyl)-6-ethylindan, 5-aminoethyl-6-methoxylindan, 5-aminoethyl-6-methoxyindan, 5-(4-aminobutyl)-6-methoxyindan and 5-(3-aminopropyl)-6-propoxyindan.

Some of the acyl halides which can be used in the process are benzoyl chloride, 4-methoxybenzoyl chloride, 3,4-dimethoxybenzoyl chloride, 3,4,5-trimethoxybenzoyl chloride, phenylacetyl chloride and 3,4-dimethoxyphenylacetyl chloride.

Reaction between the 5-aminoalkyl-6-alkyl or alkoxyindan and the acyl halide to form the desired amide is readily effected by bringing the reactants together in an inert liquid reaction medium, such as benzene or toluene, in the presence of an acid binding agent, such as triethylamine, sodium carbonate or potassium bicarbonate. Heating of the mixture, such as at reflux temperature, increases the reaction rate. After the reaction is terminated, the amide reaction product can be isolated from the reaction mixture by conventional procedures.

Representative of the amides which can be produced as described from the appropriate reactants are 5-(3,4-dimethoxybenzoyl)aminoethyl-6-methylindan, 5-(3,4,5-trimethoxybenzoyl)aminoethyl-6-methylindan, 5-(4-methoxybenzoyl)aminopropyl-6-methylindan, 5-(3,4-dimethoxybenzoyl)aminobutyl-6-methoxyindan and 5-(3,4,5-triethoxybenzoyl)aminoethyl-6-ethoxyindan.

A second method of making the compounds of Formula I is to react the 5-aminoalkyl-6-alkyl or alkoxyindan with an appropriate aldehyde to form an intermediate imine or Schiff's base which can then be reduced catalytically with hydrogen at a moderate pressure and moderately elevated temperature. This process can be represented as follows:

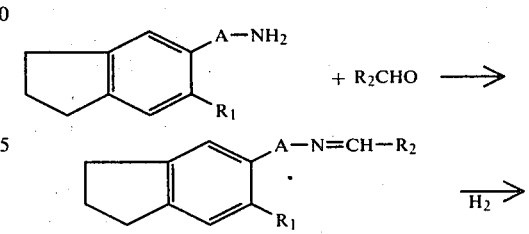

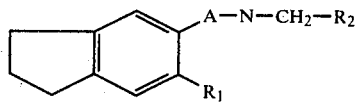

wherein A, R₁ and R₂ have the previously assigned significance.

Representative of the aldehydes which can be used in this process are benzaldehyde, 4,5-dimethoxybenzaldehyde, phenylacetaldehyde, 4-methoxybenzaldehyde, 3,4,5-triethoxybenzaldehyde and 4-methoxyphenylacetaldehyde.

Some of the Schiff's bases or imines which are produced as intermediates in the described process are 5-(N-benzylidenylaminoethyl)-6-methylindan, 5-(N-3,4-dimethoxybenzylidenylaminopropyl)-6-methoxyindan and 5-(N-3,4,5-trimethoxybenzylidenylaminoethyl)-6methoxyindan.

Reduction of the intermediate imines can be readily effected by catalytic hydrogenation at moderate pressures using platinum oxide or palladium as the catalyst and a suitable liquid carrier such as glacial acetic acid at room temperature or a moderately elevated temperature, such as up to 50° C. Following completion of the hydrogen uptake, the reaction mixture can be handled in a conventional way to isolate the desired tertiary amine. Secondary amines such as the following can be produced by this process:
5-(3,4-dimethoxybenzyl)aminoethyl-6-methylindan,
5-(4-methoxybenzyl)aminoethyl-6-methylindan,
5-(3,4,5-trimethoxybenzyl)aminoethyl-6-methylindan,
5-(4-methoxybenzyl)aminopropyl-6-methoxyindan, and
5-(3,4-diethoxybenzyl)aminobutyl-6-ethoxyindan.

The amines provided by this invention can be converted to acid addition salts by contacting the amines with a suitable inorganic acid such as hydrochloric acid, sulfuric acid, phosphoric acid and hydrobromic acid, or an organic acid such as citric acid, acetic acid, formic acid, malic acid, fumaric acid, succinic acid, benzoic acid and tartaric acid.

According to a further aspect of the invention, it has been found that the compounds of Formula I provided by this invention, that are sufficiently safe and effective, as well as the old compound 5-aminoethyl-6-methylindan, are useful pharmaceutically. These compounds, as the base or acid addition salt, when administered to animals parenterally or orally, exert an anti-hypertensive effect. The compounds are accordingly useful in reducing blood pressure.

The amount of active ingredient administered may be varied; however, it is necessary that the amount of active ingredient be such that a suitable dosage is given. The selected dosage depends upon the desired therapeutic effect and the duration of treatment. Dosages of from 0.1 to 100 mg/kg of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg of active agent.

A typical tablet can have the composition:

|  | Mg |
|---|---|
| Active agent (1) | 100 |
| Starch U.S.P. | 57 |
| Lactose U.S.P. | 73 |
| Talc U.S.P. | 9 |
| Stearic acid | 12 |

(1) 5-(3,4-dimethoxybenzyl)aminoethyl-6-methylindan

The compounds exhibit both oral and parenteral activity and accordingly they can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art, such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

The following Table 1 provides acute toxicity data and cardiovascular activity in rats for specific compounds provided by the invention, for compounds known to have anti-hypertensive activity and for a control. The Roman numerals in the first column of Table 1 coincide with the same Roman numerals adjacent the name of the compounds in the subsequent examples.

TABLE 1

Acute Toxicity in Mice and Cardiovascular Activity in Desoxycorticosterone Hypertensive Rats of N-Substituded Aminoethylindans

| Compound | Mouse n(Mice) | Mouse ALD$_{50}$, mg/kg ip | Dose, mg/kg ip | n(Rats) | Controls[a] | Mean Change in Pressure and Heart Rate from Control ± SE[b] 1 hr | 2 hr | 4 hr | 24 hr |
|---|---|---|---|---|---|---|---|---|---|
| I | 10 | >1000* | 100* | 6 | 200 ± 8 (393 ± 23) | −18 ± 8** (−20 ± 23) | −24 ± 7** (+9 ± 30) | −12 ± 6 (−14 ± 18) | −13 ± 4** (−67 ± 22**) |
| II | 10 | >1000* | 100* | 6 | 210 ± 14 (353 ± 12) | −27 ± 8** (+23 ± 28) | −35 ± 13** (+10 ± 28) | −12 ± 8 (+47 ± 29) | −16 ± 4 (−4 ± 10) |
| III | 12 | 1000-1500* | 100* | 6 | 206 ± 11 (382 ± 19) | −32 ± 7** (+13 ± 12) | −24 ± 5** (+54 ± 25) | −21 ± 4** (+19 ± 21) | −13 ± 4** (+61 ± 12**) |
| IV | 15 | 500-1000* | 100* | 6 | 202 ± 8 (389 ± 29) | −10 ± 4** (+23 ± 29) | −10 ± 2** (+57 ± 31) | −19 ± 3** (+14 ± 12) | −19 ± 4** (−27 ± 2**) |
| V | 42 | 79-89[c] | 10[c] | 6 | 181 ± 6 (299 ± 13) | −24 ± 8** (+32 ± 17) | −24 ± 4** (+34 ± 14) | −15 ± 5** (+25 ± 11) | −6 ± 4 (−4 ± 11) |
|  |  |  | 25[c] | 6 | 185 ± 6 (349 ± 22) | —[d] | —[d] | −18 ± 4** (+20 ± 21) | −11 ± 2** (−26 ± 14) |
| VI | 6 | >1000* | 100* | 5 | 179 ± 10 (325 ± 7) | −7 ± 7 (+17 ± 17) | −2 ± 6 (+24 ± 11) | −1 ± 7 (+23 ± 13) | −3 ± 10 (+2 ± 17) |
| VII | 6 | >1000* | 100* | 6 | 195 ± 8 (354 ± 19) | −2 ± 6 (+43 ± 10**) | −4 ± 9 (+47 ± 12**) | +2 ± 5 (+37 ± 15**) | −3 ± 7 (+22 ± 12) |
| VIII | 20 | 140-178* | 100* | 6 | 186 ± 6 (366 ± 16) | −58 ± 4** (−55 ± 17**) | −60 ± 7** (0 ± 14) | −47 ± 2** (+4 ± 8) | −17 ± 2** (−14 ± 10) |
| 0.9% NaCl | — | — | 1 ml/kg | 12 | 183 ± 8 (351 ± 14) | +5 ± 4 (+18 ± 12) | +4 ± 3 (+25 ± 14) | −2 ± 3 (+6 ± 6) | 0 ± 3 (0 ± 14) |
| Methyldopa | — | — | 50* | 6 | 205 ± 9 (378 ± 22) | −31 ± 4** (+106 ± 26**) | −50 ± 4** (+104 ± 28**) | −48 ± 6** (+31 ± 39) | −16 ± 5** (−19 ± 12) |
| Guanethidine | — | — | 10[c] | 5 | 197 ± 11 (427 ± 27) | −25 ± 8** (−67 ± 28**) | −46 ± 9** (−101 ± 24**) | −44 ± 6** (−95 ± 22*) | −27 ± 6** (−81 ± 26**) |

[a] Mean systolic blood pressure (mm Hg) ± SE. Numbers in parentheses represent mean heart rate (beats per minute) ± SE.
[b] Mean difference in systolic blood pressure from control (mm Hg) ± SE. Numbers in parentheses represent mean difference in heart rate from control (beats per minute) ± SE.
* Administered as a suspension in 1% tragacanth.
** Significant change from control, $p < 0.05$, by Newman-Keuls a posteriori test.
[c] Administered as a solution in distilled water.
[d] No readings possible at this time period, no perceptible pulse; respiration and movement artifacts.

Biological Methods—Acute toxicity determinations were performed in female Swiss-Webster mice, 15–24 g. Compounds were administered in aqueous solutions or as suspensions in 1% tragacanth by the intraperitoneal route to groups of three or more mice. The LD$_{50}$ values were estimated from the results obtained by administering two or more dose levels of each compound, usually spaced 0.3 logarithmic interval or less, to these groups of mice. Animals were observed for up to 72 hours following injection, but the toxicity values reported in Table 1 represent the outcome 24 hours after administration.

The indirect measurements of blood pressure and heart rate were determined in male Charles River rats made hypertensive (systolic blood pressure >159 mm Hg) by subcutaneously implanting a wax-formulated pellet containing 10 mg of desoxycorticosterone acetate. Systolic blood pressure was measured in the caudal arteries of prewarmed (40° C.), unanesthetized, restrained animals by a pneumatic pulse transducer placed distal to an automated tail pressure cuff and was recorded on a physiograph. Heart rate was determined from the amplified pulse waves recorded during the blood pressure measurements. Prior to the actual experiments, animals were accustomed to the measurement handling procedure several times during the preceding weeks.

Control systolic blood pressure and heart rates were determined in a group of usually six hypertensive rats on each day. A compound for evaluation was administered by intraperitoneal injection either in solution or as a suspension at 24 hr. intervals following injection. Mean values of the group for these parameters at a particular measurement period were calculated, and then the mean difference from control, along with its associated standard error, was calculated for each period. The statistical significance of the changes produced by a compound was tested by an analysis of variance and the Newman-Keuls a posteriori test when F was significant. A probability level of 0.05 or less was accepted as a significant change.

All compounds synthesized in this series, except V, were tested at a dosage level of 100 mg/kg. Compound V was relatively more toxic in the mouse, and it was evaluated at two lower dosage levels, 10 and 25 mg/kg. Methyldopa and guanethidine sulfate, two known antihypertensive agents, were included as reference standards. Another group of hypertensive rats was injected with 0.9% NaCl in a dose of 1 ml/kg. The latter group was included as a placebo group for the entire study.

Hypertensive rats receiving a placebo injection of 0.9% NaCl showed no significant changes in systolic blood pressure or heart rate at any time. Methyldopa and guanethidine sulfate, as expected, produced significant depressions in mean systolic blood pressure from control levels.

The following examples are presented to further illustrate the invention.

EXAMPLE 1

N-(3,4-Dimethoxyphenylacetyl)-5-aminoethyl-6-methylindan (VII)

3,4-Dimethoxyphenylacetic acid (6.47 g, 0.033 mole) was dissolved in 50 ml of dry benzene and refluxed for 2 hr. with excess thionyl chloride (25 ml). The solvent and SOCl$_2$ were removed on a rotary evaporator. Two additional quantities of dry benzene were added to the residue, followed by rotary evaporation which yielded 3,4-dimethoxyphenylacetyl chloride.

5-Aminoethyl-6-methylindan (4.0 g, 0.029 mole) was dissolved in 100 ml of dry benzene, 4 ml of triethylamine was added and a solution of the previously prepared 3,4-dimethoxyphenylacetyl chloride in dry benzene was added to the substituted indan mixture. The reaction mixture was refluxed for several hours and then gently heated overnight at a temperature below reflux. The reaction was then cooled, washed with 3×100 ml of 20% HCl solution, 3×100 ml of 8% NaHCO$_3$ solution and 2×125 ml of water. The benzene layer was then reduced in volume on a rotary evaporator to yield a solid precipitate. The solid was filtered, washed with benzene, air dried to yield a slightly pink powder (3.5 g, mp 144°–145° C.). The crude product was then recrystallized from benzene (large volume), mp 144°–144.5° C.

Anal. Calcd for $C_{22}H_{27}NO_3$ C, 74.75; H, 7.69; N, 3.96. Found: C, 74.53; H, 7.46; N, 3.90.

EXAMPLE 2

5-Benzoylaminoethyl-6-methoxyindan (I)

The procedure of Example 1 was followed in reacting 5-aminoethyl-6-methylindan with benzoylchloride, using sodium carbonate in place of triethylamine, to produce the desired product. After recrystallization from ether the product melted at 104°–106° C.

Calcd. for $C_{19}H_{21}NO_2$ C, 77.26; H, 7.17; N, 4.74; Found: C, 77.42; H, 7.26; N, 4.70.

EXAMPLE 3

5-(3,4,5-Trimethoxybenzoyl)aminoethyl-6-methoxyindan (II)

By following the procedure of Example 1, the desired product was produced by reacting 5-aminoethyl-6-methylindan with 3,4,5-trimethoxybenzoylchloride, and using sodium carbonate in place of triethylamine. After recrystallization from ethylacetate the product had a melting point of 144°–145° C.

Calcd. for $C_{22}H_{27}NO_5$ C, 68.55; H, 7.06; N, 3.63; Found: C, 68.71; H, 6.93; N, 3.61.

EXAMPLE 4

5-Phenylacetylaminoethyl-6-methoxyindan (III)

Using the procedure of Example 1, but with potassium bicarbonate replacing triethylamine, phenylacetyl chloride was reacted with 5-aminoethyl-6-methoxyindan to produce the desired product. After recrystallization from ether it had a melting point of 135° C.

Calcd. for $C_{20}H_{23}NO_2$ C, 77.63; H, 7.51; N, 4.52; Found: C, 77.48; H, 7.55; N, 4.49.

EXAMPLE 5

5-(3,4-Dimethoxyphenylacetyl)aminoethyl-6-methoxyindan (IV)

5-Aminoethyl-6-methoxyindan and 3,4-dimethoxyphenylacetyl chloride were reacted following the procedure of Example 1, except that potassium bicarbonate was used in place of triethylamine, to produce the desired product. After recrystallization from ethanol it melted at 115° C.

Calcd. for $C_{22}H_{27}NO_4$ C, 71.51; H, 7.38; N, 3.79; Found: C, 71.52; H, 7.45; N, 3.78.

EXAMPLE 6

5-Phenylacetyl-6-methylindan (VI)

Phenylacetyl chloride was reacted with 5-aminoethyl-6-methylindan to produce the desired product. After recrystallization from benzene it melted at 125.5°–127° C.

Calcd. for $C_{20}H_{23}NO$ C, 81.87; H, 7.90; N, 4.77; Found: C, 81.68; H, 8.07; N, 5.08.

EXAMPLE 7

N-(3,4-Dimethoxybenzyl)-5-aminoethyl-6-methylindan hydrochloride (VIII)

5-Aminoethyl-6-methylindan (4.0 g, 0.0228 mole) was dissolved in 125 ml of benzene and added slowly (dropwise) to a refluxing solution of 3,4-dimethoxybenzaldehyde in 150 ml of benzene. Distilling benzene was caught in a Dean Stark trap. Approximately 125 ml of benzene was run off over a period of 4 hr. The remaining benzene solution was refluxed overnight. Two further 25 ml quantities of benzene were removed via the Dean Stark trap. Rotary evaporation of the remaining benzene solution yielded the intermediate imine as an oil (7.7 g).

The crude imine was dissolved in 60 ml of glacial acetic acid and hydrogenated at 45 psi of hydrogen at room temperature over 0.5 g of platinum oxide catalyst. When hydrogen uptake ceased, the catalyst was filtered through a Celite filter aid. The filtrate was cooled by the addition of ice and a cooled solution of 60 g of NaOH in 400 ml of water was added. The precipitated product (oily solid) was extracted from the mixture with 3×130 ml of ether. The combined ether extracts were dried over anhydrous $Na_2SO_4$ and then evaporated to yield the desired compound as the free base as a moderately viscous pale orange oil.

The hydrochloride salt was prepared by dissolving the free base in diisopropyl ether (anhydrous) and bubbling HCl gas through the solution until no further precipitation occurred. The precipitated salt was filtered, dried and recrystallized from acetonitrile/ethanol to yield the title compound as shiny colorless needles, mp 223°–224° C.

Anal. Calcd for $C_{21}H_{28}ClNO_2$. C, 69.69; H, 7.79; Cl, 9.97; N, 3.87. Found: C, 69.63; H, 7.96; Cl, 9.75; N, 3.87.

EXAMPLE 8

5-Aminoethyl-6-methylindan HCl (V)

This compound, as the base, is old and is disclosed in J. Org. Chem; 39, 2852 (1974). The HCl salt is readily prepared by conventional methods. When recrystallized from cold dilute hydrochloric acid it had a melting point of 229°–231° C.

The foregoing detailed description has been given for clearness of understanding only, and no unnecessary limitations should be understood therefrom as modifications will be obvious to those skilled in the art.

What is claimed is:

1. A compound of the formula

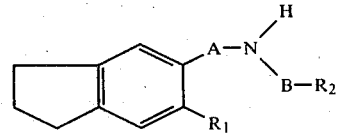

wherein A represents an alkylene group having 2 to 5 carbons in a straight chain, $R_1$ represents a lower alkyl having 1 to 3 carbons or is a lower alkoxy having 1 to 3 carbons, B represents —$CH_2$— or

and $R_2$ represents phenyl or phenyl-lower alkyl and the phenyl group in such substituents is unsubstituted or is substituted with 1 to 3 lower alkoxy groups, and acid addition salts of the amines.

2. A compound according to claim 1 in which $R_1$ is methoxy, A is ethylene, B is

and $R_2$ is phenyl.

3. A compound according to claim 1 in which $R_1$ is methoxy, A is ethylene, B is

and $R_2$ is 3,4,5-trimethoxyphenyl.

4. A compound according to claim 1 in which $R_1$ is methoxy, A is ethylene, B is

and $R_2$ is benzyl.

5. A compound according to claim 1 in which $R_1$ is methoxy, A is ethylene, B is

and $R_2$ is dimethoxybenzyl.

6. A compound according to claim 1 in which $R_1$ is methyl, A is ethylene, B is

and $R_2$ is benzyl.

7. A compound according to claim 1 in which $R_1$ is methyl, A is ethylene, B is

and $R_2$ is 3,4-dimethoxybenzyl.

8. A compound according to claim 1 in which $R_1$ is methyl, A is ethylene, B is —$CH_2$— and $R_2$ is 3,4-dimethoxyphenyl.

9. A method which comprises administering a compound as defined in claim 1, or 5-aminoethyl-6-methylindan, to an animal afflicted with high blood pressure in an amount sufficient to lower the animal's blood pressure.

10. A pharmaceutical composition, for treating an animal afflicted with high blood pressure, containing 2 to 300 mg. of a compound as defined in claim 1 or of 5-aminoethyl-6-methylindan, and an inert pharmaceutically acceptable carrier.

11. A method which comprises orally administering a compound as defined in claim 1, or 5-aminoethyl-6-methylindan, to an animal afflicted with high blood pressure in an amount sufficient to lower the animal's blood pressure.

12. A method which comprises parenterally administering a compound as defined in claim 1, or 5-aminoethyl-6-methylindan, to an animal afflicted with high blood pressure in an amount sufficient to lower the animal's blood pressure.

* * * * *